United States Patent [19]

Lutz et al.

[11] Patent Number: 4,527,988

[45] Date of Patent: Jul. 9, 1985

[54] POROUS CONTRACEPTIVE DEVICE WITH AN INTERSTITIAL LIQUID

[76] Inventors: Peter L. Lutz, 561 Satinwood Dr., Miami, Fla. 33149; Joseph D. Richard, 3647 St. Gaudens Rd., Miami, Fla. 33133

[21] Appl. No.: 420,325

[22] Filed: Sep. 20, 1982

[51] Int. Cl.³ .............................. A61F 5/44
[52] U.S. Cl. ................................. 604/349
[58] Field of Search ............ 604/349, 323, 335; 128/760, 132 R, 138 R; 383/102, 103; 428/131, 315.5; 168/1 R

[56] References Cited

U.S. PATENT DOCUMENTS

| | | | |
|---|---|---|---|
| 2,371,883 | 3/1945 | Gammeter et al. | 604/349 |
| 2,512,872 | 6/1950 | Penska | 604/349 |
| 2,904,041 | 9/1959 | Brown | 128/132 R |
| 3,677,225 | 7/1972 | Czively | 128/132 R |
| 3,932,682 | 1/1976 | Loft et al. | 428/315.5 |

FOREIGN PATENT DOCUMENTS 641521  8/1928  France ................. 604/349

*Primary Examiner*—C. Fred Rosenbaum
*Assistant Examiner*—J. L. Kruter

[57] ABSTRACT

An improved contraceptive device comprising a condom of conventional shape and material such as latex. A large number of small holes in the condom allow the transfer of hormonal, pheromonal, and other bio-active fluids during sexual intercourse. The cross sectional diameter of the holes is made small enough to impede the passage of human spermatozoa so that the contraceptive function is retained.

3 Claims, 2 Drawing Figures

POROUS CONTRACEPTIVE DEVICE WITH AN INTERSTITIAL LIQUID

BACKGROUND OF THE INVENTION

Although latex condoms are less expensive and more convenient to use, the relatively more expensive condoms made of animal membranes, such as sheep intestine, are still widely used throughout the world. In fact, they are preferred by the cognocenti despite their several disadvantages. The widespread preferance for these so called "natural skins" is generally attributed to their superior thermal conductivity. However, thermodynamic considerations indicate that an appreciable temperature gradient across even a relatively thick latex condom can persist for only a very brief period after intromission. This observation, along with recent research findings, has led us to the more rational conclusion that the enhanced sensitivity of natural membrane condoms is largely, if not solely, attributable to their permeability. Thus, the diffusion of one or more bio-active fluids, possibly including pheromones, through the natural membrane provides the subtle yet widely appreciated sensory advantage over impermeable latex. The object of this invention is to provide a condom of artificial material such as latex which has all the advantages of permeability while still retaining the contraceptive function.

SUMMARY OF THE INVENTION

The present invention provides an improved condom of latex or other suitable material which is made artifically permeable by the inclusion of a large number of small uniformly sized holes. The cross sectional diameter of the holes is kept small enough to impede the passage of human spermatozoa, while at the same time allowing the diffusion of at least some of the bio-active fluids secreted during sexual intercourse. Because of the small size of the human spermatozoon, conventional methods of punching holes in elastic material are unsuitable for this application. In the preferred method of making contraceptive devices according to the present invention, a low power pulsed laser is used to burn (or ablate) small and uniformly sized holes in the condom, preferably while it is still mounted on the forming mandrel.

DESCRIPTION OF THE PREFERRED EMBODIMENT

Figure 1:
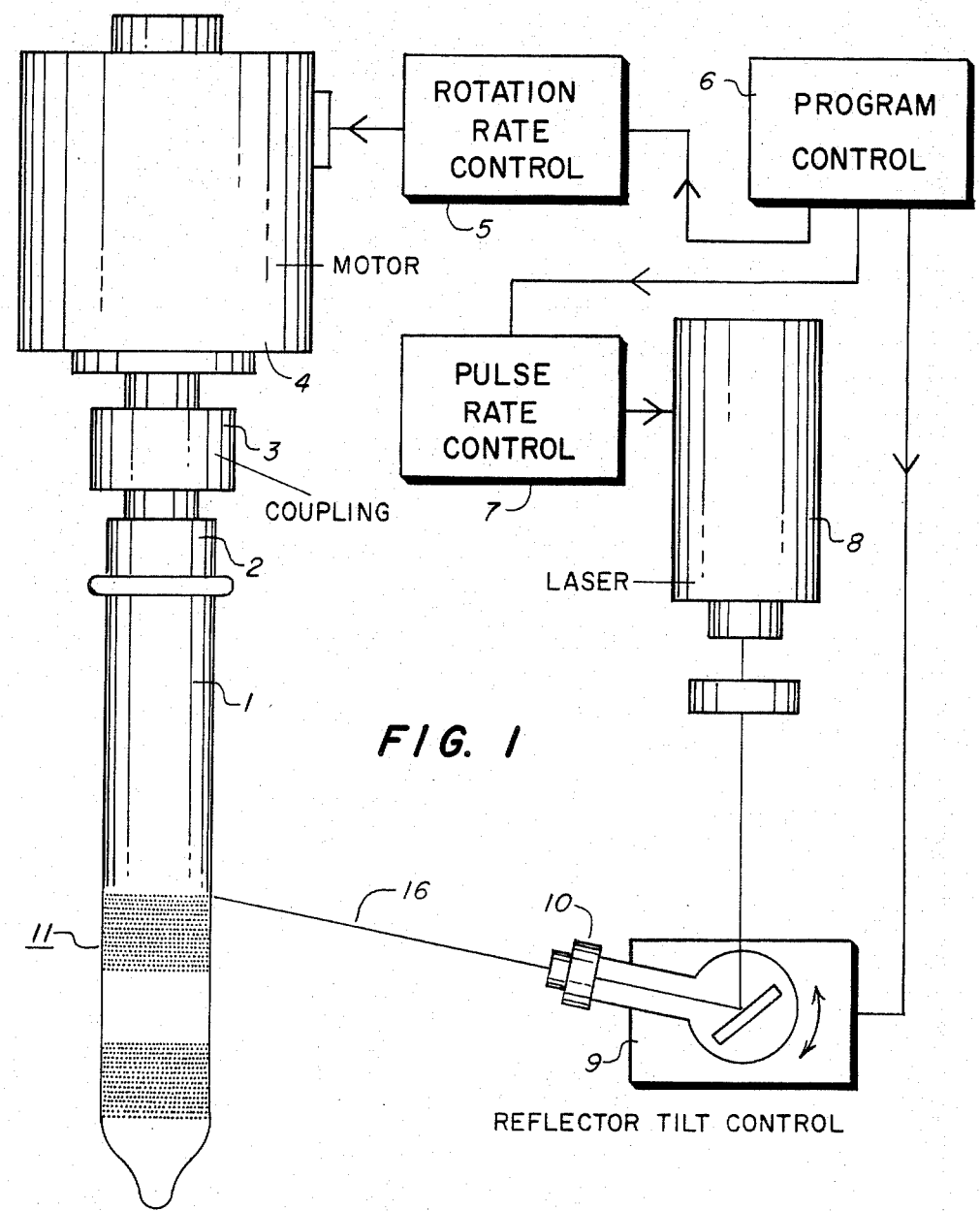
FIG. 1 is a schematic representation of a preferred method for making small and uniformly sized holes in a condom of synthetic material according to the present invention.

In FIG. 1, a condom 1 of synthetic material, such as latex, is shown on a forming mandrel 2 which is temporarily coupled to the motor 4 by means of the coupling 3. The rotation rate of motor 4 is controlled by the program control 6 and the rotation rate control 5. The program control 6 also controls the pulse rate of the laser 8 by means of the pulse rate control 7. The laser beam 16 is deflected through a changing angle by means of the reflector tilt control 9 in a predetermined time relationship with the aforementioned motor rotation rate and laser pulse rate. Final focus of the laser beam 16 is effected by the focus control 10. Thus the rotation rate of the mandred 2, the laser pulse rate, and the angular tilt rate of the laser beam reflector are all synchronously controlled by the program control 6 so that a helical pattern of uniformly spaced holes 11 is burned (or ablated) in the wall of the condom 1.

The technique of using laser pulses and a synchronously deflected laser beam to produce a large number of precisely sized and uniformly spaced holes in a rotating ablatable surface will be familiar to those skilled in the art. Previously, the technique has been used to record information on an optical disk memory. Recently, variations of the same technique have been used to record video and audio information on disks. In such applications, the requirements for high laser pulse rate, narrow beam focus (typically to produce a hole size less than one micrometer in diameter), hole size uniformity, and precise spacings between holes have all been more exacting than those required to produce porous condoms according to the present invention. Since pulsed laser technology has already developed far beyond the requirements of the present application and is familiar to those skilled in the art, any more technical description of the pulsed laser of FIG. 1 would be superfluous.

Figure 2:
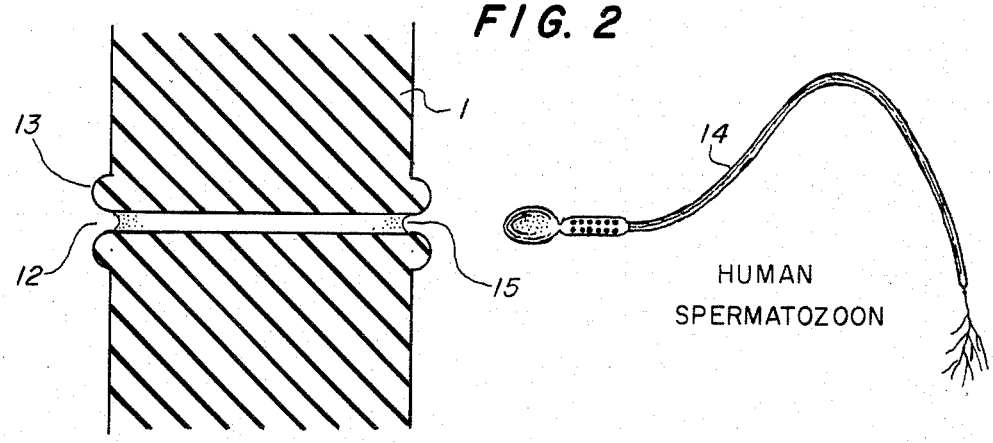
FIG. 2 shows the size of relationships between a human spermatozoon and one of the small diameter holes in the wall of the condom shown in FIG. 1.

In FIG. 2, a hole 12 is shown in the wall of the condom 1. When the hole 12 is burned (or ablated) through the condom wall by means of a laser pulse as shown in FIG. 1, the molten material forms a toroidal rim 13 around the opening of each hole. An aqueous solution 15 is shown filling most of the space within the hole 12. The aqueous solution in the hole 12 facilitates the diffusion of other fluids through the hole. The holes are filled with the aqueous solution by subjecting the porous surface of the condom to the solution, and the process can be expedited by the use of either pressure or vacuum to force the fluid into the holes. For size comparison, a human spermatozoon 14 is shown adjacent the fluid filled hole 12.

Although a hole 12 diameter of about 2 micrometers (microns) diameter is shown in FIG. 2 to prevent the passage of the relatively larger spermatozoon 14, holes of considerably larger diameter can also be effective in impeding passage because the spermatozoon does not propel itself in a sinuous or serpentine manner but, instead, it relies on wide lateral sweeps of its long posterior flagellum for mobility. Therefore, porous condoms according to the present invention can include holes of relatively larger diameter while still retaining an effective contraceptive function.

Obviously, the degree of porosity of a condom according to the present invention can vary widely depending only in the hole diameter and the total number of holes. For example, the porous condom shown in FIG. 1 contains 120,000 holes each of 2 microns diameter. The holes are in a helical pattern and the hole spacing is 100 microns between holes in each turn, and 500 microns between adjacent turns (rings), so that 100 helical turns are contained in a 5 cm section of the condom. Alternatively a much larger number of holes can be provided to increase the porosity.

From the foregoing it will be seen that the present invention provides a porous condom of synthetic material which has at least some of the advantages of condoms made of animal membranes. Although a particular condom shape and pattern of holes is shown in the drawing for purposes of illustration, many alternatives to the details shown are possible. For example, as an alternative to the use of a simple aqueous solution with a wetting agent in the pores to facilitate diffusion of other fluids, a spermacide can be added to increase the contraceptive safety factor. Alternatively, other aqueous solutions (or other liquids) can be used to fill the holes in the porous condom. As a further alternative, the fluid within the holes can be omitted entirely.

As an alternative to the use of a reflector tilt control as shown in FIG. 1, a screw drive mechanism can be used to move the mandrel 2 and condom 1 axially as they are rotated by the motor 4. It can be readily seen that if the condom moves along its axis in a predetermined synchronous relationship with its rotation, the same helical pattern of holes can be formed while the laser beam 16 remains motionless. This alternative would eliminate the need for the reflector tilt control while increasing somewhat the complexity of the motor drive mechanism.

What is claimed is:

1. A permeable contraceptive device comprising a condom at a thin flexible synthetic material having a wall portion with a plurality of regularly open spaced holes which are of a uniform size and cross-sectional diameter in said condom wall and which are sufficiently small to prevent the passage of spermatozoon through said openings in said condom wall and further has a interstitial liquid within the open holes.

2. A permeable contraceptive device as described in claim 1 wherein said interstitial fluid also contains a spermacide.

3. A permeable contraceptive device as described in claim 1 wherein said holes are uniformly spaced in a substantially circular pattern around the circumference of said condom.

* * * * *